United States Patent [19]

Scholz

[11] Patent Number: 5,567,618
[45] Date of Patent: Oct. 22, 1996

[54] KARL FISCHER REAGENT

[75] Inventor: Eugen Scholz, Garbsen, Germany

[73] Assignee: Riedel-De Haen Aktiengesellschaft, Germany

[21] Appl. No.: 445,210

[22] Filed: May 18, 1995

[30] Foreign Application Priority Data

Jun. 18, 1994 [DE] Germany ............... 44 21 453.7

[51] Int. Cl.⁶ .................................................. G01N 33/18
[52] U.S. Cl. ........................... 436/42; 436/60; 205/788; 204/405
[58] Field of Search ............... 436/39–42, 60; 204/153.22, 405; 205/788, 788.5

[56] References Cited

U.S. PATENT DOCUMENTS

| | | | |
|---|---|---|---|
| 4,378,972 | 4/1983 | Scholz | 436/42 |
| 4,429,048 | 1/1984 | Scholz | 436/42 |
| 4,550,083 | 10/1985 | Fischer et al. | 436/42 |
| 4,578,483 | 3/1986 | Mabelis | 549/297 |
| 4,619,900 | 10/1986 | Scholz | 436/42 |
| 4,647,542 | 3/1987 | Fischer et al. | 436/42 |
| 4,703,014 | 10/1987 | Fischer et al. | 436/42 |
| 4,720,464 | 1/1988 | Kuwata et al. | 436/42 |
| 4,740,471 | 4/1988 | Scholz | 436/42 |
| 4,748,126 | 5/1988 | Fischer et al. | 436/42 |
| 4,802,957 | 2/1989 | Kuwata et al. | 204/1 T |
| 4,874,709 | 10/1989 | Fischer et al. | 436/42 |
| 5,102,804 | 4/1992 | Fisher et al. | 436/42 |
| 5,139,955 | 8/1992 | Scholz | 436/42 |
| 5,187,101 | 2/1993 | Kato et al. | 436/42 |
| 5,292,413 | 3/1994 | Scholz | 204/153.22 |
| 5,466,606 | 11/1995 | Scholz | 436/42 |

FOREIGN PATENT DOCUMENTS

| | | |
|---|---|---|
| 135098 | 3/1985 | European Pat. Off. . |
| 299310 | 1/1989 | European Pat. Off. . |
| 384195 | 8/1990 | European Pat. Off. . |
| 3614135 | 11/1986 | Germany . |

OTHER PUBLICATIONS

Analytical Chemistry, Bd. 63, Nr. 10, May 15, 1991, pp. 557a–566a.

*Primary Examiner*—Jill Warden
*Assistant Examiner*—Harold Y. Pyon
*Attorney, Agent, or Firm*—Connolly & Hutz

[57] ABSTRACT

The present invention relates to a Karl Fischer reagent for the determination of water, characterized in that it contains tetrahydrofurfuryl alcohol (THFA) as alcohol component.

18 Claims, No Drawings

KARL FISCHER REAGENT

The present invention relates to a Karl Fischer reagent for the determination of water, which reagent contains tetrahydrofurfuryl alcohol (THFA) as alcohol component.

In the Karl Fischer titration, water is determined by a redox titration. According to the reaction equation

$$H_2O + I_2 + [RNH]SO_3R' + 2\ RN \rightarrow [RNH]SO_4 + 2[RNH]I$$

where RN is a base and R' is a substituted or unsubstituted alkyl, an alkyl ester of sulphurous acid is oxidized by iodine. This consumes a stoichiometric amount of water. In practice, alkyl esters of methanol or of 2-methoxyethanol (methyl glycol) are used (E. Scholz, "Karl Fischer Titration", Springer-Verlag, 1984).

The alcohol used influences the Karl Fischer reagent and the Karl Fischer titration being carried out therewith in various ways. It has an effect on the stability of the reagent, the speed of the titration and the stoichiometry. Depending on the way the Karl Fischer titration is carried out, the individual factors are of different importance.

In practice, the Karl Fischer titration is carried out in various forms, namely volumetrically or coulometrically. In the volumetric titration, there are two variants, the single-component and the two-component reagent.

In the case of the single-component reagent, all reactive components, viz. iodine, sulphur dioxide, the base and the alcohol, are present in one solution. The sulphur dioxide is here present as alkyl sulphite, i.e. it has reacted with the alcohol during the preparation. Karl Fischer recommended methanol as alcohol. Later Peters and Jungnickel recommended 2-methoxyethanol as solvent. Other alcohols are not usual in practice. The disadvantage is that all single-component reagents show a fall-off in normality.

In the determination of water using the single-component reagent, the sample to be analysed is dissolved in methanol or a methanol-containing solvent mixture and titrated with the reagent. In other alcohols the titration proceeds too slowly or non-stoichiometrically.

The two-component reagent for volumetric analysis comprises a solvent component and a titrant component. The latter is an alcoholic iodine solution. The solvent component is prepared from alcohol, the base and the sulphur dioxide. Here too, the sulphur dioxide reacts with the alcohol to form the alkyl sulphite. Both solutions are stable on storage. The alcohol used in the two-component reagents is virtually exclusively methanol.

In the titration using the two-component reagent, the sample is dissolved in the methanolic solvent component or in mixtures of the solvent component with other organic solvents. This solution is then titrated with the titrant component.

The coulometric determination can be carried out with or without a diaphragm. The solution used contains sulphur dioxide, the base, an alcohol and a dissolved iodide. Here too, the sulphur dioxide is present as alkyl sulphite. In the titration, iodine is generated from the iodide by anodic oxidation, and the iodine then reacts with the water in the known manner. In coulometry too, methanol is the preferred alcohol. All other alcohols give too low a conductivity of the anolyte.

The alcohols hitherto customary have certain disadvantages. Methanol is toxic. Furthermore, the stability of the single-component reagents is very unsatisfactory. The normality falls off by about 1% per day. For this reason, single-component reagents are hardly used any more nowadays. Mention should also be made of side reactions with some substances to be analysed, such as, for example, the alkylation of aromatic amines, etherification with silanols, acetal formation with aldehydes. However, methanol has a very good solvent capability for many substances, for the samples to be analysed, for the components of the Karl Fischer reagent and for the reaction products thereof. For this reason, methanol is the preferred solvent for the sample.

2-Methoxyethanol is teratogenic and foetotoxic and for this reason should actually not be used for laboratory purposes. In addition, in the Karl Fischer reagents it reacts so slowly that methanol or another alcohol has to be used as solvent for the sample. If aldehydes are titrated in the presence of a large amount of 2-methoxyethanol, the so-called bisulphite addition, in which water is bound, occurs. The water values found are thereby falsified: they are too low. An advantage is the improved stability of the single-component reagents prepared using 2-methoxyethanol. The fall-off in normality is only about 1% per month.

It is an object of the present invention to find an alcohol which avoids the disadvantages of the two customary alcohols. Surprisingly, tetrahydrofurfuryl alcohol (THFA) has been found to be particularly suitable.

The present invention accordingly provides a Karl Fischer reagent for the determination of water, characterized in that it contains tetrahydrofurfuryl alcohol (THFA) as alcohol component.

The Karl Fischer reagent of the invention can be in the form of a single-component or two-component system for volumetric analysis or as a reagent for coulometry. The Karl Fischer reagent of the invention contains, besides the tetrahydrofurfuryl alcohol, the customary constituents of a KF reagent, in particular sulphur dioxide, a base such as but not limited to a nitrogen containing base, such as but not limited to pyridine, imidazole, diethanolamine or salts of carboxylic acids and iodine or iodide.

The Karl Fischer reagent of the invention contains the specified constituents in the customary amounts known to those skilled in the art.

For example, the concentrations in a single-component reagent are from about 0.2 to about 3 mol/l of sulphur dioxide, from about 0.2 to about 6 mol/l of base and from about 0.05 to about 1 mol/l of iodine.

A solvent component contains, for example, from about 0.2 to about 3 mol/l of sulphur dioxide and from about 0.2 to about 6 mol/l of base. A titrant component contains, for example, from about 0.03 to about 1 mol/l of iodine.

A reagent of the invention for coulometric determination of water contains, for example, from about 0.2 to about 3 mol/l of sulphur dioxide, from about 0.2 to about 5 mol/l of base and from about 0.01 to about 0.5 mol/l of iodide.

Besides the specified constituents, the Karl Fischer reagent of the invention can also contain further customary constituents or auxiliaries which, for example, improve the solubility of the samples or increase the conductivity of coulometric reagents. The Karl-Fischer reagent of the invention has, in practice, some unexpected advantages. The single-component reagents prepared using THFA are more stable than the comparable reagent solutions using 2-methoxyethanol. The fall-off in normality is only 0.5% per month.

The determinations of water proceed rapidly in THFA, so that this alcohol can also be used as solvent for the sample. Thus, it is also possible to carry out titrations in which THFA is used as solvent for the sample and also as reactant in the single-component reagent. This makes possible determinations of water in which methanol is completely excluded. Side reactions with aromatic amines or silanols are thus completely suppressed. Acetal formation with aromatic aldehydes is retarded to such an extent that it no longer interferes in the determination of water, so that even relatively large amounts of aromatic aldehydes can be titrated, which is the prerequisite for the determination of traces of water. The bisulphite addition which occurs with 2-methoxyethanol, cannot be detected with THFA. THFA can therefore be used both as reactive components in reagents and also as solvent for the sample. For this reason, two-component reagents can also be prepared using THFA and used for the titration.

THFA is also suitable for coulometric reagents. The reagents prepared therewith have a higher conductivity than reagents using 2-methoxyethanol.

THFA can also be used in combination with other solvents or alcohols. Single-component reagents can be prepared with addition of 2-methoxyethanol, chloroform or aromatic hydrocarbons if this appears to be advantageous in particular cases. In the titration using a single-component reagent containing THFA, methanol can be used as solvent for the sample as before. Alternatively, it is also possible to use mixtures of solvents, as required by the sample to be analysed. Examples are mixtures of methanol and chloroform or of methanol and long-chain aliphatic alcohols for the titration of fats, mixtures of methanol and formamide for the analysis of sugars or a mixture of THFA with N-methylformamide for the determination of water in aromatic aldehydes.

In the case of two-component reagents, both components can be prepared using THFA. They can also contain different solvents. The combined use with conventional solvent or titrant components is possible. Thus, for example, titrant components containing xylene as solvent can be used if the titrant is to be made less hygroscopic. Likewise, additions of chloroform to the solvent component are possible if the solvent capability for long-chain hydrocarbons is to be improved.

For coulometry, it is possible to prepare anolytes which, in the usual manner, contain a base, sulphur dioxide, an iodide and THFA. Further additives are possible, for example the addition of substances which increase the electrolytic conductivity (quaternary ammonium salts) or which increase the solvent capability for the samples to be analysed (formamide, N-methylformamide).

Such a reagent can be used in a coulometric titration cell in a known manner. If the cell consists of 2 chambers which are separated by a diaphragm or an ion exchange membrane, the reagent is introduced into the anode space. The cathode space can be charged with a commercial or another suitable catholyte. In a single-chamber cell, the cell is charged with the reagent of the invention.

EXAMPLE 1

A single-component reagent is prepared by dissolving 170 g of imidazole (2.5 mol) in 700 ml of THFA. 100 g of sulphur dioxide (1.56 mol) and 100 g of iodine (0.79 mol) are then added. The mixture is made up to 1 liter with THFA.

EXAMPLE 2

A single-component reagent is prepared in a similar manner to Example 1, using 316 g of pyridine. (4 mol) in place of the imidazole.

EXAMPLE 3

A solvent component for a two-component reagent is prepared by dissolving 100 g of imidazole (1.47 mol) and 50 g of sulphur dioxide (0.78 tool) in THFA to a total volume of 1 liter.

EXAMPLE 4

A solvent component for a two-component reagent is prepared by dissolving 105 g of diethanolamine (1 mol) and 64 g of sulphur dioxide (1 mol) in THFA to a total volume of 1 liter.

EXAMPLE 5

A titrant component for a two-component reagent is prepared by dissolving 70 g of iodine in THFA to a total volume of 1 liter.

EXAMPLE 6

1 liter of anolyte for coulometric determination is prepared by dissolving 68 g of imidazole (1 mol), 40 g of sulphur dioxide (0.62 mol) and 60 g of imidazole hydrobromide (0.4 mol) in the appropriate amount of THFA. 39 g of iodine (0.3 mol) are then added and reduced to iodide by addition of a little water.

EXAMPLE 7

1 liter of anolyte for coulometric determination is prepared by dissolving 50 g of imidazole (0.73 mol), 40 g of sulphur dioxide (0.62 mol), 60 g of imidazole hydrobromide (0.4 mol) and 60 g of imidazole hydroiodide (0.3 mol) in 600 ml of N-methylformamide and 200 ml of THFA. The solution is then made up to 1 liter using N-methylformamide and sufficient iodine is added to eliminate the water present in the raw materials.

Use Examples

The use examples correspond to the basic forms of the Karl Fischer titration customary nowadays. In the volumetric determination using a single-component reagent, the titration vessel is initially charged with a suitable solvent (usually methanol). The sample is then added and titrated with the Karl Fischer reagent. In the case of the two-component reagent, the solvent component is initially charged and titration is carried out using the titrant component. Prior to the addition of the sample, the solvent or the solvent component can be titrated dry in a pre titration. Otherwise, the water content of the initial charge is separately determined and taken into account mathematically.

In coulometry, the titration cell of a commercially manufactured coulometer is charged with the Karl Fischer reagent. After switching on the apparatus, the cell is dried automatically. The sample is then added and analysed in accordance with the directions for the titration apparatus.

Use Example 1

The volumetric titration cell is initially charged with methanol. The sample to be analysed is dissolved therein and the water content is titrated using a titrant in accordance with Example 1 or Example 2.

Use Example 2

The volumetric titration cell is initially charged with THFA and titrated dry using a titrant in accordance with Example 1 or Example 2. The sample is then added and dissolved in the THFA. The water content is then titrated using the same titrant.

Use Example 3

The volumetric titration cell is initially charged with THFA. The sample to be analysed is then added. The water content is titrated using a commercial single-component reagent in accordance with the German Pharmacopoeia 10.

Use Example 4

The volumetric titration cell is initially charged with the solvent component in accordance with Example 3. The water-containing sample is added and titrated using the titrant component in accordance with Example 5.

Use Example 5

The volumetric titration cell is initially charged with the solvent component in accordance with Example 4. The water-containing sample is added and titrated using a Commercial titrant component which is a solution of 65 g of iodine in 1 liter of methanol.

Use Example 6

The volumetric titration cell is initially charged with a commercial solvent component, e.g. a solution of 120 g of pyridine and 60 g of sulphur dioxide in methanol. The sample to be analysed is added. The water content is titrated using a titrant component in accordance with Example 5.

Use Example 7

In a commercial coulometer possessing a 2-chamber cell, the anode space and the cathode space are charged with the reagent in accordance with Example 6. Using this reagent, the water content is determined in the manner prescribed for the apparatus.

Use Example 8

A commercial Karl Fischer coulometer having a cell with one chamber is charged with the reagent in accordance with Example 7. The water content is determined in the manner appropriate to the apparatus.

We claim:

1. Karl Fischer reagent for the determination of water, comprising a base, sulfur dioxide, iodine or iodide, and tetrahydrofurfuryl alcohol (THFA) as an alcohol component.

2. The Karl Fischer reagent according to claim 1, wherein said reagent is a single-component reagent which further comprises sulphur dioxide, a base and iodine.

3. The Karl Fischer reagent according to claim 2, which further comprises at least two different solvents.

4. The Karl Fischer reagent according to claim 2, wherein said base is pyridine; imidazole, diethanolamine or a salt of a carboxylic acid.

5. The Karl Fischer reagent according to claim 1, said regent is a two-component reagent comprising a solvent component and a titrant component.

6. The Karl Fischer reagent according to claim 5, wherein said titrant component comprises alcohol and iodine.

7. The Karl Fischer reagent according to claim 5, wherein said titrant component comprises methanol and iodine.

8. The Karl Fischer reagent according to claim 5, which further comprises at least two different solvents.

9. The Karl Fischer reagent according to claim 5, said solvent component contains THFA, sulphur dioxide and a base.

10. The Karl Fischer reagent according to claim 9, wherein said base is pyridine, imidazole, diethanolamine or a salt of a carboxylic acid.

11. The Karl Fischer reagent according to claim 9, wherein said titrant component comprises methanol and iodine.

12. The Karl Fischer reagent according to claim 11, wherein said base is pyridine, imidazole, diethanolamine or a salt of a carboxylic acid.

13. The Karl Fischer reagent according to claim 1, for the coulometric determination of water, which comprises sulphur dioxide, a base and iodide.

14. The Karl Fischer reagent according to claim 13, which further comprises an auxiliary to improve the conductivity.

15. The Karl Fischer reagent according to claim 13, wherein said base is pyridine, imidazole, diethanolamine or a salt of a carboxylic acid.

16. The Karl Fischer reagent according to claim 13, which further comprises at least two different solvents.

17. A method for the quantitative determination of water in a water-containing sample, comprising mixing said water-containing sample with a solvent and then titrating with a Fischer reagent as claimed in claim 1, said sample.

18. A method for the quantitative determination of water in a water-containing sample, comprising mixing said water-containing sample with a solvent, titrating said sample with a Karl Fischer reagent, wherein said Karl Fischer reagent comprises a nitrogen containing base mixed with tetrahydrofurfuryl alcohol, sulphur dioxide and iodine and calculating the quantity of water in said sample based upon said quantity of Karl Fischer reagent consumed.

* * * * *